United States Patent [19]

Takaishi et al.

[11] 3,976,708

[45] Aug. 24, 1976

[54] PROCESS FOR THE PREPARATION OF TRICYCLO[5.3.1.0$^{3,8}$]UNDERCANE

[75] Inventors: Naotake Takaishi, Iwademachi; Yoshiaki Inamoto, Wakayama; Kiyoshi Tsuchihashi, Kainan, all of Japan

[73] Assignee: Kao Soap Co., Ltd., Tokyo, Japan

[22] Filed: May 23, 1975

[21] Appl. No.: 580,183

[30] Foreign Application Priority Data

May 31, 1974 Japan.............................. 49-62231

[52] U.S. Cl...................... 260/666 PY; 260/666 M
[51] Int. Cl.$^2$......................................... C07C 13/54
[58] Field of Search................. 260/666 PY, 666 M

[56] References Cited
OTHER PUBLICATIONS

Krautz, et al., Chem. Lommuu., 1971, 1287.

Krautz, et al., J. Amer. Chem. Soc., 95, 5662, 1973.

Schleyer, et al., Chem. Letters, 1189, 1973.

N. S. Vorobieva, D. A. Arefiev, V. I. Epshev, and A. A. Petrov, Chem. Ab., 75:19562e, [Neftekhimiya 11,163, 1971].

Naotake Takaishi et al., J. Org. Chem. 40 No. 3, pp. 276–281, 1975.

*Primary Examiner*—Veronica O'Keefe
*Attorney, Agent, or Firm*—Woodhams, Blanchard and Flynn

[57] ABSTRACT

A process for the preparation of tricyclo[5.3.1.0$^{3,8}$]-undecane which comprises isomerizing 6,7-exo-trimethylenebicyclo[3.2.1]octane in the presence of an acid catalyst.

5 Claims, No Drawings

PROCESS FOR THE PREPARATION OF TRICYCLO[5.3.1.0³·⁸]UNDERCANE

BACKGROUND OF THE INVENTION

1. FIELD OF THE INVENTION

This invention relates to a process for preparing tricyclo[5.3.1.0³·⁸]undecane by isomerizing 6,7-exo-trimethylenebicyclo[3.2.1.]octane. More particularly, this invention relates to a process for synthesizing easily a known tricyclic hydrocarbon, tricyclo[5.3.1.0³·⁸]undecane (II) (hereinafter sometimes referred to as "4-homoisotwistane"), by catalytically isomerizing 6,7-exo-trimethylenebicyclo[3.2.1]octane (I) as shown in the following reaction scheme (1):

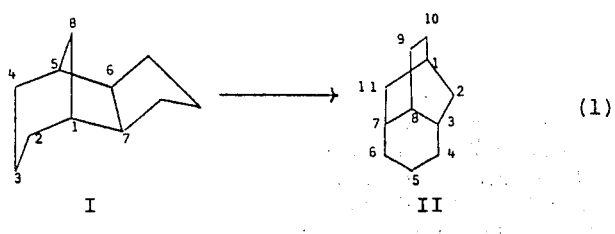

2. DESCRIPTION OF THE PRIOR ART

It was previously found by N. S. Vorobieva, O. A. Arefiev, V. I. Epishev and A. A. Petrov that when 6,7-exo-trimethylenebicyclo[3.2.1]octane (I) is isomerized in the presence of an aluminum halide, 1- and 2-methyladamantanes can be obtained (Neftekhimiya, 11, 163 (1971)).

We have investigated the catalytic isomerization of a variety of polycyclic hydrocarbons in the presence of acid catalysts. Isomerization of 6,7-exo-trimethylenebicyclo[3.2.1]octane (I) was examined in detail as one specific embodiment of such catalytic isomerization. As a result, it was found that in an intermediate stage of that isomerization normally leading to formation of 1- and 2-methyladamantanes as final products, a number of reaction intermediates including 4-homoisotwistane (II) are formed. These intermediates are formed at various stages of consecutive and competitive reactions starting from 6,7-exo-trimethylenebicyclo[3.2.1]octane (I) during the complicated course of these combined reactions. When the reaction is stopped partway to completion, a mixture is obtained containing variable proportions of these intermediates, depending on the reaction conditions and/or the reaction time. We found that if the reaction conditions, such as the type and amount of the catalyst, the reaction solvent, the reaction temperature and the reaction time, are appropriately chosen, the proportion of 4-homoisotwistane (II) in such intermediate mixture can be increased. This isomerization reaction can be utilized for the synthesis of 4-homoisotwistane (II), which is a known useful substance. Based on this finding, we have now completed this invention.

2. SUMMARY OF THE INVENTION

In accordance with this invention, there is provided a process for synthesizing 4-homoisotwistane (II), which comprises isomerizing 6,7-exo-trimethylenebicyclo[3.2.1]octane (I) under limited reaction conditions to form a reaction mixture containing as the main component 4-homoisotwistane (II), and separating and recovering the desired compound (II) from this mixture.

As noted above, 6,7-exo-trimethylenebicyclo[3.2.1]octane (I) used as the starting substance in this invention is a known compound which can be transformed to 1- and 2-methyladamantanes, after passing through various reaction intermediates. Accordingly, in order to obtain in a high yield the desired 4-homoisotwistane (II), which is one of these reaction intermediates, it is necessary to perform the reaction under limited reaction conditions. The term "under limited reaction conditions" means an isomerization reaction which is brought to an end at an appropriate time, an isomerization reaction which is conducted in the presence of a small amount of a catalyst or in the presence of a catalyst having a relatively low acidity, an isomerization reaction which is conducted in a solvent, an isomerization reaction which is carried out at a relatively low temperature, or an isomerization reaction which is carried out under a suitable combination of the foregoing conditions. The isomerization reaction under limited reaction conditions, according to the invention, is carried out so that the isomerization reaction is stopped at a stage at which the content of tricyclo[5.3.1.0³·⁸]undecane (II) in the reaction mixture is at least about 30 weight percent, and is preferably at the highest level that can be attained under the reaction conditions which is usually up to about 60 weight percent.

In contrast, when the isomerization reaction is carried out under severe conditions such as the use of a strong Lewis acid catalyst, for example, aluminum halides and antimony pentahalides, in an amount of more than 50 mole percent based on the starting substance (I), the absence of a solvent and a reaction temperature exceeding about 50°C., the starting substance (I) is rapidly isomerized to the final 1- and 2-methyladamantanes and it is substantially impossible to detect intermediates including 4-homoisotwistane (II), the desired product of this invention.

In order to establish such limited reaction conditions, there can be used as catalyst Brønsted acids, for example, sulfuric acid, fluorosulfonic acid, chlorosulfonic acid, alkanesulfonic acids such as methanesulfonic acid, trifluoromethanesulfonic acid and ethanesulfonic acid, and arenesulfonic acids such as benzenesulfonic acid and p-toluenesulfonic acid. The amount of such Brønsted acid catalysts can be from 0.1 to 1000 moles, preferably from 1 to 100 moles, per one mole of starting substance (I). In addition there can be used as catalyst Lewis acids such as aluminum halides, boron trifluoride and antimony pentahalides, provided that the amount of said Lewis acid catalyst is from 0.01 to 0.5 moles, per one mole of the starting substance (I). As the halides, it is preferred to use the chlorides and bromides.

In order to complete the reaction in a short time, it is permissible to use a Brønsted acid in an equivalent amount or in molar excess, but in the case of a Lewis

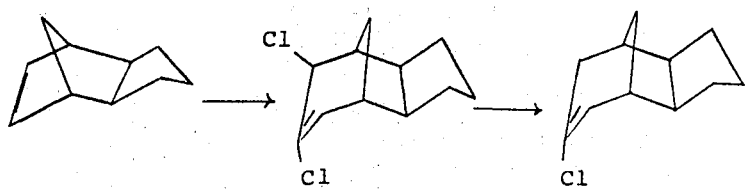

acid, in order to prevent the reaction from progressing too rapidly, the amount used of the Lewis acid should be smaller than 50 mole percent based on the starting substance.

It is possible to use a mixture comprising two or more of the foregoing acid catalysts, and in the case of some specific combinations, for example, sulfuric acid-boron trifluoride, a synergistic effect can be obtained.

In the process of this invention, advantageously good results are obtained when a solvent is used, in addition to the above selection of the amount and kind of the catalyst. The type of solvent used is not critical. Any members of the classes of aromatic hydrocarbons, aliphatic hydrocarbons, halogenated hydrocarbons and ethers can be used as solvent, provided that it is inert to the catalyst used. These solvents can be used in combination with either a Bronsted acid or a Lewis acid. The amount of the solvent is from 0.1 to 500 times the weight of the starting material (I).

In the process of this invention, the isomerization is carried out at a temperature ranging from −30° to +100°C., but it is preferred that the reaction be carried out at −10° to +50°C.

As pointed out above, N. S. Vorobieva, O. A. Arefiev, V. I. Epishev and A. A. Petrov apparently first synthesized 6,7-exo-trimethylenebicyclo[3.2.1]octane (I), the starting substance of this invention, and used it for the isomerization reaction (see the reference mentioned above), but that reference does not describe a specific process for the synthesis of this compound.

We confirmed that the compound (I) can be synthesized by any of the several processes described below. Namely, 6,7-exo-trimethylenebicyclo[3.2.1]octane (I) can be obtained, for example, by enlarging the ring of 5,6-exo-trimethylenenorbornan-2-one (III) with diazomethane and subjecting the resulting 6,7-exo-trimethylenebicyclo[3.2.1]octan-3-one (IV) to the Wolf-Kischner reduction according to the method of DeBoer et al (Org. Syntheses Coll., vol IV, 225) as shown in the following reaction scheme (2):

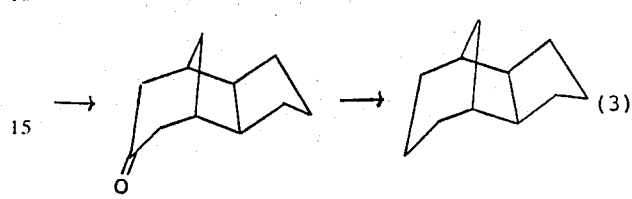

4-Homoisotwistane (II) prepared by the process of this invention is a compound having a tricyclic basket-like molecular structure, analogous to that of adamantane. In addition to the known utility of 4-homotwistane for preparing 1-methyladamantane, it and its derivatives are useful for pharmaceutical purposes, especially as anti-viral agents, and also are useful as lubricity-improving additives to lubricating oils and fiber-treating oils, as well as surface active agents and the like because of the inherent physical and chemical properties of polycyclic hydrocarbons.

This invention will now be further described in detail by reference to the following illustrative Examples. In addition, processes for the synthesis of 6,7-exo-trimethylenebicyclo[3.2.1]octane (I), the starting substance of this invention, are described in the following Preparations.

Preparation 1

A 500 ml-capacity four-necked round-bottomed flask was charged with 26.8 g (0.2 mole) of 5,6-exo-trimethylene-norbornene-2 (V) synthesized according to the process of Youngblood et al (J. Org. Chem., 21, 1436 (1956)) and 150 ml of petroleum ether, and 40 g (0.74 mole) of sodium methylate was added thereto. While the mixture was being agitated on an ice-sodium chloride bath, 126 g (0.65 mole) of ethyl trichloroacetate was added dropwise to the mixture over a period of 3 hours so that the temperature of the reaction mixture did not exceed 0°C. After completion of the dropwise

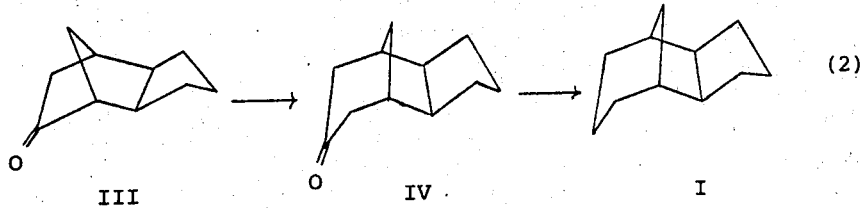

Alternatively, compound (I) can be obtained by reducing 6,7-exo-trimethylenebicyclo[3.2.1]octan-3-one (IV) derived from a reaction product formed by ring-enlarged 5,6-exo-trimethylene-norbornene-2 (V) with dichlorocarbene according to the process of Jefford et al (Org. Syntheses, 51, 60 (1971)) as shown in the following reaction scheme (3):

addition, the mixture was further agitated at a temperature not exceeding 0°C. for 4 hours, and the temperature was gradually elevated to room temperature and the mixture was further agitated overnight. The reaction mixture was added to a mixture of 150 g of ice and 100 ml of water. The separated aqueous layer was extracted with diethyl ether 4 times using 60 ml of diethyl ether each time, and the aqueous layer was neutralized with 20 percent hydrochloric acid and extracted with diethyl ether two times by using 60 ml of ether each time. The ether extracts were combined with the organic layer, and the mixture was washed with a saturated aqueous solution of sodium chloride, dried with anhydrous sodium sulfate and fractionated.

A fraction boiling at 138° to 140°C. under 5 mm Hg was recovered to obtain 22.5 g (yield = 50%) of 3,4-dichloro-6,7-exo-trimethylenebicyclo[3.2.1]oct-2-ene (VI).

Elemental Analysis Values: Found: C = 60.5%, H = 6.6%, Cl = 32.8% Calculated as $C_{11}H_{14}Cl_2$: C = 60.85%, H = 6.50%, Cl = 32.65% ir(cm$^{-1}$) 2945, 2850, 1621, 1319, 1050, 958, 798, 693 ms (m/e) (relative intensity, %): 218 (3), 216 (4), 115 (14), 114 (9), 113 (41), 112 (17), 77 (29), 69 (100), 68 (15), 67 (19), 41 (14)

$^1$Hnmr (CDCl$_3$ solvent): δ6.12 (doublet, 1H,

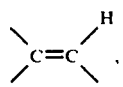

7.0 Hz), δ4.15 (doublet, 1 H,

δ3.0 – 0.9 (complex multiplet, 12H)

A 1 l-capacity round-bottomed flask was charged with 6.45 g (0.17 mole) of lithium aluminum hydride, 150 ml of dry diethyl ether and 450 ml of dry tetrahydrofuran, and a solution of 20.6 g (0.095 mole) of the above-obtained 3,4-dichloro-6,7-exo-trimethylenebicyclo[3.2.1]oct-2-ene (VI) in 20 ml of tetrahydrofuran was added dropwise under agitation over a period of 30 minutes. Then, the mixture was slowly refluxed for 22 hours and allowed to cool to room temperature (20°–25°C.). The remaining lithium aluminum hydride was decomposed by carefully adding water to the reaction mixture, and the reaction mixture was placed in 300 g of ice water. The water layer was made acidic (pH = 5 to 6) by addition of 10 percent hydrochloric acid and extracted with diethyl ether 5 times using 100 ml of ether each time. The ether extracts were combined with the organic layer, and the mixture was washed with 100 ml of a saturated aqueous solution of sodium chloride, dried with anhydrous sodium sulfate and fractionated.

A fraction boiling at 77° to 79°C. under 2 mm Hg was recovered to obtain 11.8 g (yield = 68%) of 3-chloro-6,7-exo-trimethylenebicyclo[3.2.1]oct-2-ene (VII).

Elemental Analysis Values: Found: C = 72.5%, H = 8.1%, Cl = 19.4% Calculated as $C_{11}H_{15}Cl$: C = 72.32%, H = 8.28%, Cl = 19.40% ir(cm$^{-1}$): 3045, 2935, 2855, 1640, 1465, 1310, 1035, 957, 850, 680 ms (m/e) (relative intensity,%): 182 (25), 115 (35), 114 (44), 113 (100), 112 (91), 79 (56), 77 (48), 69 (30), 41 (27)

$^1$Hnmr (CDCl$_3$ solvent): δ6.0 (doublet, 1H, -CH=C<, J-7 Hz), δ 2.8–0.8 (complex multiplet, 14H)

A 200 ml-capacity round-bottomed flask was charged with 80.0 ml of concentrated sulfuric acid, and 7.3 g (0.04 mole) of the above-obtained 3-chloro-6,7-exo-trimethylenebicyclo[3.2.1]oct-2-ene (VII) was added at one time under ice cooling and agitation. The temperature was gradually elevated to room temperature and the mixture was agitated overnight. The reaction mixture was placed on 200 g of broken ice pieces under agitation and extracted with diethyl ether 3 times by using 150 ml of diethyl ether each time. The combined ether layers were washed with water, dried with anhydrous sodium sulfate and fractionated. A fraction boiling at 75° to 77°C. under 0.5 mm Hg was recovered to obtain 3.6 g (yield = 55%) of 6,7-exo-trimethylenebicyclo[3.2.1]oct-3-one (IV).

Elemental Analysis Values: Found: C = 80.8%, H = 10.2% Calculated as $C_{11}H_{16}$: C = 80.44%, H = 9.82% ir(cm$^{-1}$): 2945, 2850, 1703, 1645, 1408, 1210, 1065, 825 ms (m/e) (relative intensity, %): 164 (M$^+$, 74), 121 (54), 120 (86), 95 (100), 79 (57), 68 (44), 67 (82), 41 (62)

$^1$Hnmr (CDCl$_3$ solvent): δ2.5 – 0.7 (complex multiplet)

A 200 ml-capacity round-bottomed flask was charged with 11 g (0.2 mole) of potassium hydroxide and 110 ml of diethylene glycol, and 3.3 g (0.02 mole) of the above-obtained 6,7-exo-trimethylenebicyclo[3.2.1]oct-3-one (IV) and 14 ml of 80 percent hydrazine hydrate were added thereto. The mixture was heated and refluxed for 2 hours and 30 minutes, and the temperature was gradually elevated while removing distilled substances from the reaction system. Then, the mixture was agitated at 210°C. for 5 hours.

The reaction mixture was cooled to room temperature in ambient air and then added to 400 ml of cold water. The water was extracted with 100 ml of petroleum ether 5 times. The extracts were combined with the organic layer.

The organic layer was washed with a saturated aqueous solution of sodium chloride, dried with anhydrous sodium sulfate and fractionated. A fraction boiling at 63° to 65°C. under 2 mm Hg was recovered to obtain 2.4 g (yield = 79.5%) of 6,7-exo-trimethylenebicyclo[3.2.1]octane (I).

$n_D^{22}$ 1.4967

Elemental Analysis Values: Found: C = 87.9%, H =12.1% Calculated as $C_{11}H_{18}$: C = 87.92%, H = 12.08% ir(cm$^{-1}$): 2925, 2855, 1455, 1355, 1300, 1290, 1230, 1120, 1070, 970, 918 870 ms (m/e) (relative intensity, %): 150 (M$^+$, 51), 135 (13), 108 (24), 93 (22), 91 (19), 79 (50), 67 (82), 55 (25), 53 (37), 41 (100)

$^1$Hnmr (CDCl$_3$ solvent): δ0.92 – 2.3 (complex multiplet)

Preparation 2

A 300 ml-capacity round-bottomed flask was charged with 30 g (0.2 mole) of 5,6-exo-trimethylenebornan-2-one (III) synthesized according to the process of Bruson et al (J. Am. Chem. Soc., 67, 723 (1945)), 50 g (0.232 mole) of p-toluene-sulfonylmethylnitrosoamide, 60 ml of 95 percent ethanol and 4 ml of water, and while the mixture was being cooled on an ice-sodium chloride bath, a solution of 6 g of potassium hydroxide in 20 ml of 50 percent aqueous ethanol was gradually added dropwise under agitation. When 0.5 to 1 ml of the solution was added dropwise, nitrogen was formed and the temperature was elevated. The dropwise addition was continued while maintaining the temperature at 10° to 20°C. After completion of the dropwise addition, the mixture was further agitated for 30 minutes and it was then made acidic by addition of 2N hydrochloric acid.

Ethanol was removed from the reaction mixture by distillation, and the residue was extracted with petroleum ether. The ehter extract was washed with a 1 percent aqueous solution of sodium hydrogencarbonate and then with water, dried with anhydrous sodium sulfate and fractionated. A fraction boiling at 77° to 79°C. under 1 mm Hg was recovered to obtain 2.6 g (yield = 8%) of 6,7-exo-trimethylenebicyclo[3.2.1]oct-3-one. This is transformed to 6,7-exo-trimethylenebicyclo[3.2.1] octane (I) as described in Preparation 1. All of the infrared absorption spectrum, nmr spectrum and mass spectrum of the product were in agreement with those of the standard product obtained in Preparation 1.

EXAMPLE 1

A solution of 7.5 g (0.05 mole) of 6,7-exo-trimethylenebicyclo[3.2.1]octane (I) in 100 ml of methylene chloride was agitated while maintaining it at 0°C., and 15 g (0.1 mole) of trifluoromethanesulfonic acid was added to the solution. Then, the mixture was heated and refluxed under agitation for 5 hours.

The reaction mixture was cooled to room temperature in ambient air and was added to 100 ml of ice water. The organic layer was separated, and the water layer was extracted with methylene chloride. The methylene chloride extract was combined with the organic layer, and the mixture was washed with a saturated aqueous solution of sodium hydrogencarbonate and then with water, and dried with anhydrous sodium sulfate. Methylene chloride was removed by distillation and the residue was fractionated. A fraction boiling at 110° to 113°C. under 33 mm Hg was recovered to obtain 3.2 g (yield = 43%) of tricyclo[5.3.1.0$^{3,8}$]undecane (II).

Melting Point: 62° – 63°C. (sealed tube)

Elemental Analysis Values: Found: C = 87.8%, H = 12.2% Calculated as $C_{11}H_{18}$: C = 87.92%, C = 12.08% ir(cm$^{-1}$): 2925, 2890, 2870, 2850, 1480, 1465, 1450, 1440, 1340, 975, 940, 895, 845 ms (m/e) (relative intensity, %): 150 (M$^+$, 100), 122 (39), 121 (39), 109 (12), 108 (16), 107 (19), 93 (27), 81 (27), 80 (46), 79 (40), 67 (35), 55 (18), 41 (40)

$^1$Hnmr (CDCl$_3$ solvent): δ1.0 – 2.0 (complex multiplet)

$^{13}$Cnmr (CDCl$_3$ solvent, 15.1 Mhz, TMS at 0 ppm) (ppm): 15.2 24.8, 26.3 27.1. 30.9, 31.9, 32.3, 35.1

EXAMPLE 2

A solution of 7.5 g (0.05 mole) of 6,7-exo-trimethylenebicyclo[3.2.1]octane (I) in 100 ml of methylene chloride was agitated while maintaining it at 0°C., and 2 g (0.015 mole) of anhydrous aluminum chloride was added to the solution. The mixture was heated and refluxed under agitation for hours. The reaction mixture was cooled to room temperature in ambient air and was added to 100 ml of ice water. The organic layer was separated, and the aqueous layer was extracted with methylene chloride. the methylene chloride extract was combined with the organic layer, and the mixture was washed with a saturated aqueous solution of sodium hydrogencarbonate and then with water, and dried with anhydrous sodium sulfate. Methylene chloride was removed by distillation and the residue was fractionated. The highest boiling point fraction (85° to 86°C. under 10 mm Hg) was recovered to obtain 3 g (yield = 40%) of tricyclo[5.3.1.0$^{3,8}$]undecane (II). The infrared absorption spectrum, nmr spectrum and mass spectrum of the product were in agreement with those of the product (II) obtained in Example 1.

The embodiments of this invention in which an exclusive property or privilege is claimed are defined as follows:

1. A process for preparing tricyclo[5.3.1.0$^{3,8}$]undecane (II) which comprises isomerizing 6,7-exo-trimethylenebicyclo[3.2.1]octane (I), at a temperature in the range of from −30° to +100°C., in the presence of an acid catalyst selected from the group consisting of (1) at least one Brønsted acid, and (2) at least one Lewis acid in an amount of 0.01 to 0.5 mole per mole of I; terminating the isomerization reaction when the content of II in the reaction mixture is at least about 30 weight percent; and recovering II from the reaction mixture.

2. The process according to claim 1 wherein the temperature of the isomerization reaction is in the range of −10° to 50°C.

3. The process according to claim 1 in which the acid catalyst is at least one Brønsted acid selected from the group consisting of sulfuric acid, fluorosulfonic acid, chlorosulfonic acid, methanesulfonic acid, trifluoromethanesulfonic acid, ethanesulfonic acid, benzenesulfonic acid and p-toluenesulfonic acid.

4. The process of claim 1 in which the acid catalyst is at least one Lewis acid selected from the group consisting of boron trifluoride, aluminum halides and antimony halides.

5. The process of claim 1 in which the isomerization reaction is carried out in the presence of an inert solvent.

* * * * *